US012185473B2

(12) United States Patent
Berkowitz et al.

(10) Patent No.: US 12,185,473 B2
(45) Date of Patent: Dec. 31, 2024

(54) CATHETER WITH FLEXIBLE SUBSTRATE FOR MINIMIZING MAGNETIC INTERFERENCE

(71) Applicant: Biosense Webster (Israel) Ltd., Yokneam (IL)

(72) Inventors: Shemer Shmaryau Berkowitz, Binyamina (IL); Sharona Ben Shoshan, Zichron Yaacov (IL); Eden Kidishman, Modiin (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/876,191

(22) Filed: Jul. 28, 2022

(65) Prior Publication Data

US 2022/0369472 A1    Nov. 17, 2022

Related U.S. Application Data

(62) Division of application No. 15/834,623, filed on Dec. 7, 2017, now Pat. No. 11,700,695.

(51) Int. Cl.
*H05K 3/28* (2006.01)
*A61B 5/00* (2006.01)
(Continued)

(52) U.S. Cl.
CPC ............ *H05K 3/281* (2013.01); *A61B 5/062* (2013.01); *A61B 5/065* (2013.01); *A61B 5/287* (2021.01);
(Continued)

(58) Field of Classification Search
CPC ...... A61B 18/1492; A61B 2018/00351; A61B 2018/00357; A61B 2018/00577;
(Continued)

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| CN | 1732382 B | 1/2011 |
| CN | 106687168 A | 5/2017 |

(Continued)

OTHER PUBLICATIONS

International Search Report and Written Opinion mailed on Feb. 14, 2019 for PCT International Application No. PCT/IB2018/058958.
(Continued)

*Primary Examiner* — Minh N Trinh
(74) *Attorney, Agent, or Firm* — Frost Brown Todd LLP

(57) ABSTRACT

A catheter for canceling magnetic interference is disclosed. The catheter includes a catheter shaft having a distal end with sensors and a handle with electronics and non-magnetic sensors. Inside the catheter shaft is at least one flexible substrate having conductive traces. Another flexible substrate is wrapped around a component in the catheter shaft. The catheter further includes a plurality of connectors. A first connector connects the sensors to one end of the at least one flexible substrate. A third connector connects the non-magnetic sensors to one end of the other flexible substrate. A second connector and a fourth connector both connect the electronics to another end of the at least one flexible substrate.

9 Claims, 7 Drawing Sheets

(51) Int. Cl.
   *A61B 5/06* (2006.01)
   *A61B 5/287* (2021.01)
   *A61B 18/00* (2006.01)
   *A61B 18/14* (2006.01)
   *A61B 90/00* (2016.01)
   *A61M 25/00* (2006.01)
   *H01R 43/26* (2006.01)
   *H05K 1/02* (2006.01)

(52) U.S. Cl.
   CPC ........ *A61B 5/6852* (2013.01); *A61B 18/1492* (2013.01); *A61M 25/0009* (2013.01); *H01R 43/26* (2013.01); *A61B 2018/00351* (2013.01); *A61B 2018/00357* (2013.01); *A61B 2018/00577* (2013.01); *A61B 2018/00815* (2013.01); *A61B 2018/00821* (2013.01); *A61B 2018/00875* (2013.01); *A61B 2018/00982* (2013.01); *A61B 2090/065* (2016.02); *A61B 2090/3954* (2016.02); *A61B 2562/12* (2013.01); *H05K 1/028* (2013.01); *H05K 2201/051* (2013.01)

(58) Field of Classification Search
   CPC .. H01R 43/26; H05K 1/028; H05K 2201/051; H05K 3/281
   See application file for complete search history.

(56) References Cited

U.S. PATENT DOCUMENTS

| | | |
|---|---|---|
| 5,558,091 A | 9/1996 | Acker et al. |
| 5,588,432 A | 12/1996 | Crowley |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |
| 6,456,864 B1 | 9/2002 | Swanson et al. |
| 6,546,270 B1 | 4/2003 | Goldin et al. |
| 6,690,963 B2 | 2/2004 | Ben-Haim et al. |
| 6,788,967 B2 | 9/2004 | Ben-Haim et al. |
| 2007/0219551 A1 | 9/2007 | Honour et al. |
| 2009/0024015 A1 | 1/2009 | Curry |
| 2009/0093806 A1 | 4/2009 | Govari et al. |
| 2009/0138007 A1 | 5/2009 | Govari et al. |
| 2010/0057046 A1 | 3/2010 | Stevens et al. |
| 2013/0090599 A1 | 4/2013 | Mchugh |
| 2014/0104800 A1 | 4/2014 | Rotigni et al. |
| 2014/0180118 A1* | 6/2014 | Stigall .................. A61B 8/0891 600/463 |
| 2014/0276004 A1 | 9/2014 | Strupeck et al. |
| 2015/0197063 A1 | 7/2015 | Shinar et al. |
| 2016/0345857 A1 | 12/2016 | Jensrud et al. |
| 2017/0189103 A1 | 7/2017 | Beeckler et al. |
| 2019/0175056 A1 | 6/2019 | Berkowitz |
| 2022/0369472 A1* | 11/2022 | Berkowitz ........... A61B 5/6852 |

FOREIGN PATENT DOCUMENTS

| | | |
|---|---|---|
| WO | 2014/124231 A1 | 8/2014 |
| WO | 2015/116687 A1 | 8/2015 |
| WO | 2016/130713 A1 | 8/2016 |

OTHER PUBLICATIONS

Chinese First Office Action and Search Report dated Dec. 28, 2023, for Application No. 201880078976.7, 10 pages.
Chinese Second Office Action dated Mar. 13, 2024, for Application No. 201880078976.7, 10 pages.
Japanese First Office Action dated Nov. 8, 2022, for Application No. 2020-530962, 6 pages.
Japanese Final Office Action dated Jun. 27, 2023, for Application No. 2020-530962, 1 page.

* cited by examiner

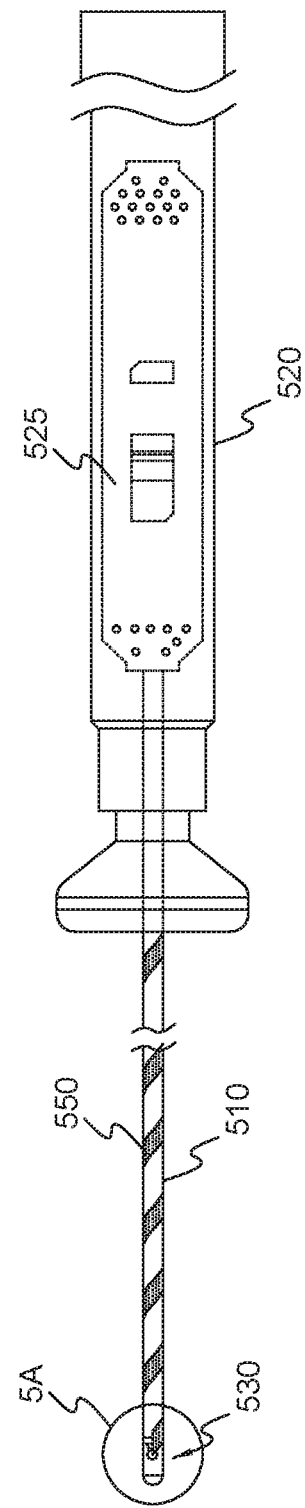
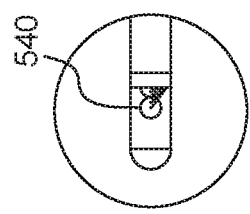
FIG. 5A
FIG. 5

CATHETER WITH FLEXIBLE SUBSTRATE FOR MINIMIZING MAGNETIC INTERFERENCE

CROSS REFERENCE TO RELATED APPLICATION

This application is a division of U.S. patent application Ser. No. 15/834,623, filed Dec. 7, 2017, now U.S. Pat. No. 11,700,695, which issued Jul. 11, 2023, which is incorporated by reference as if fully set forth.

SUMMARY

A catheter and method for catheter assembly are disclosed. A flexible substrate includes a number of layers, where each layer has a number of printed wires. The wires are printed on the flexible substrate using a conductive material. The printed substrate is environmentally protected. The printed substrate is rolled and inserted into the catheter. Connectors are attached to each end of the substrate. The connectors are in turn connected to sensors at a distal end of the catheter and with electrical cards or a cable connector at a proximate or handle end of the catheter. At least one layer of the substrate is connected to a coil in a magnetic sensor, for example. In an implementation, a reference layer is used to determine or measure magnetic radiation for interference purposes by connecting and/or shorting two traces in the reference layer at a distal end of the catheter. These measurements are used by a processor or hardware to cancel out the magnetic interference effect on the other layers. In an implementation, another printed substrate can be wrapped around the catheter shaft and used for non-magnetic type sensors.

BRIEF DESCRIPTION OF THE DRAWINGS

A more detailed understanding may be had from the following description, given by way of example in conjunction with the accompanying drawings wherein:

FIG. 5 is an example printed ribbon wrapped around a catheter in accordance with certain implementations;

FIG. 5A is an exploded view of an end of the printed ribbon shown in FIG. 5.

DETAILED DESCRIPTION

Figure 1:
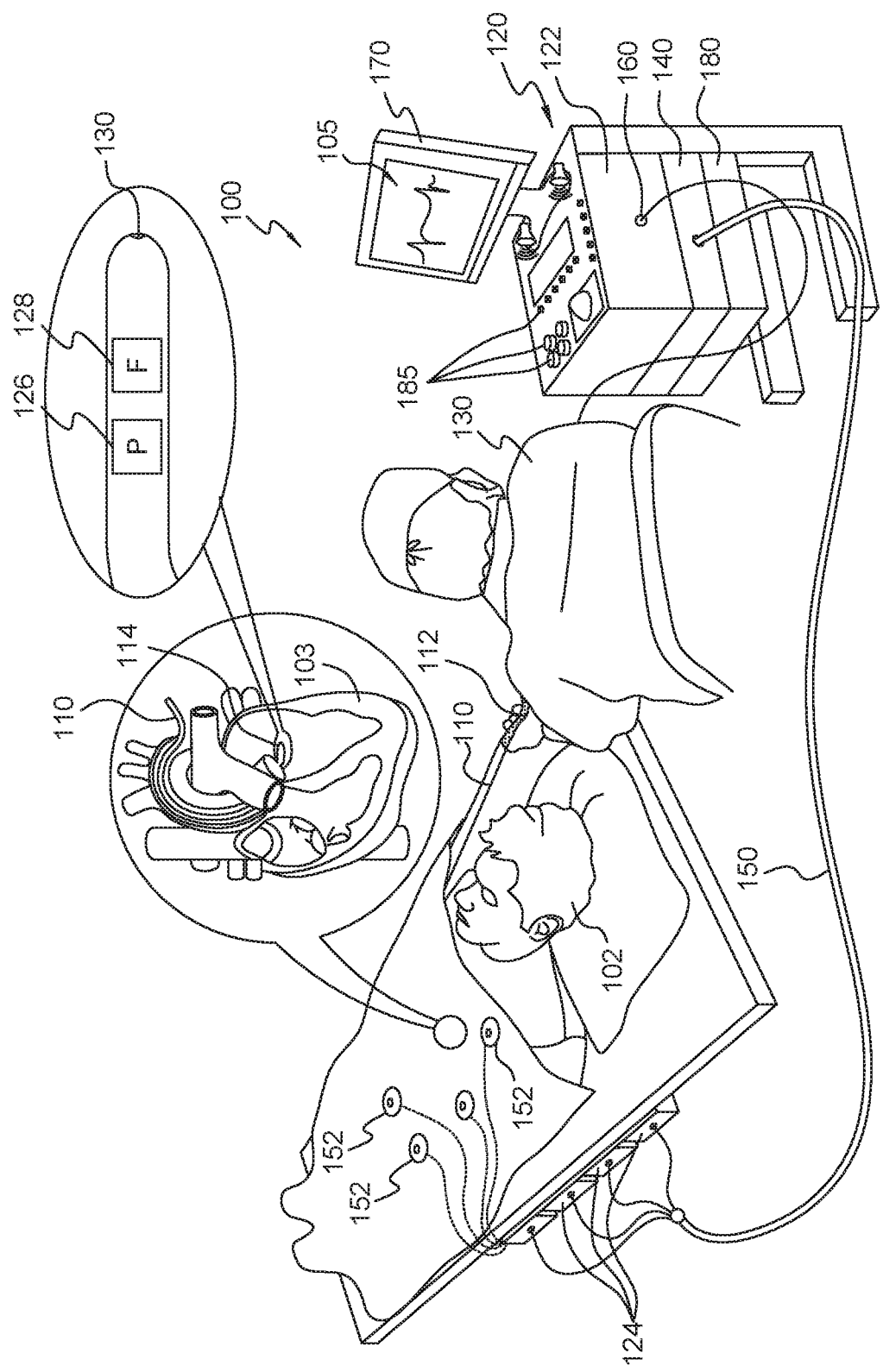
FIG. 1 is a high level schematic, pictorial illustration of a medical system in accordance with certain implementations.

Documents incorporated by reference in the present patent application may include terms that are defined in a manner that conflict with the definitions made explicitly or implicitly in the present specification. In the event of any conflicts, the definitions in the present specification should be considered to be controlling.

Cardiac ablation is a medical procedure performed by electrophysiologists that may be used to correct heart rhythm defects, known as arrhythmias, by creating lesions to destroy tissue in the heart that contributes to the rhythm defects. An example arrhythmia that can be treated using cardiac ablation is atrial fibrillation (AF), which is an abnormal heart rhythm that originates in the atria of the heart. Goals of cardiac ablation are to remove the arrhythmia to return the patient's heart to a normal heart rhythm or reduce the frequency of arrhythmia and the severity of symptoms in the patient.

Cardiac ablation may employ long, flexible catheters (endoscope) that may be inserted through a small incision in the groin and through the blood vessels to the heart, and may be used to apply energy (e.g., radio frequency (RF) energy, or extreme cold) to produce small scars or lesions on the tissue to block faulty electrical impulses that may cause the heart rhythm disorders. These lesions, also called transmural lesions, are scar tissue that penetrates the heart tissue and keeps errant electrical signals from being transmitted Current methods for manufacturing the catheter shaft are extremely cumbersome. Catheter shafts contain a large (and increasing) number of wires with electrodes. Each wire is pulled through the catheter shaft and then soldered into place. This is labor intensive and time consuming as there can be dozens of wires that need to be soldered on both the proximal and distal ends of the catheter shaft. Moreover, this method is prone to human error in properly terminating both ends of each conductor to its proper respective termination point.

Described herein is a catheter and method for catheter assembly. In general, a flexible substrate or ribbon includes a number of layers, where each layer has a number of printed wires. The wires are printed on the flexible substrate using a conductive material. The printed substrate is environmentally protected by lamination or other similar techniques. The printed substrate is inserted into the catheter. In an implementation, the printed substrate is rolled prior to insertion. In an implementation, the printed substrate is maintained in a straight line format prior to insertion. Connectors are attached to each end of the substrate. The connectors are in turn connected to sensors at a distal end of the catheter and with electrical cards or a cable connector at a proximate or handle end of the catheter. In an implementation, a layer is connected to a coil in a magnetic sensor, for example. In an implementation, a reference layer is used to determine or measure magnetic radiation for interference purposes. For example, the reference layer is shorted to measure magnetic radiation interference. These measurements are used by a processor or hardware to cancel out the magnetic interference effect on the other layers. In an implementation, another printed substrate can be wrapped around the catheter shaft and used for non-magnetic type sensors.

FIG. 1 is an illustration of an example medical system 100 that is used to generate and display information during a medical procedure and to control the deployment of various catheters within a subject. Example system 100 includes a catheter 110, such as an intracardiac catheter, a console 120 and an associated catheter control unit 112. As described herein, it will be understood that catheter 110 is used for diagnostic or therapeutic treatment, such as for example, mapping electrical potentials in a heart 103 of a patient 102 or performing an ablation procedure. Alternatively, catheter 110 can be used, mutatis mutandis, for other therapeutic and/or diagnostic purposes in heart 103, lungs, or in other body organs and ear, nose, and throat (ENT) procedures.

An operator 130 can, for example, insert catheter 110 into the vascular system of patient 102 using catheter control unit 112 so that a distal end 114 of catheter 110 enters a chamber of the patient's heart 103. Console 210 can use magnetic position sensing to determine position coordinates of distal end 114 inside heart 103. To determine the position coordinates, a driver circuit 122 in console 120 may drive field generators 124 to generate magnetic fields within the body of patient 102. Field generators 124 can include coils that may be placed below the torso of the patient 103 at known positions external to patient 103. These coils may generate magnetic fields in a predefined working volume that contains heart 103.

A location sensor 126 within distal end 114 of catheter 110 can generate electrical signals in response to these magnetic fields. A signal processor 140 can process these signals in order to determine the position coordinates of distal end 114, including both location and orientation coordinates. Known methods of position sensing described hereinabove are implemented in the CARTO™ mapping system produced by Biosense Webster Inc., of Diamond Bar, Calif., and is described in detail in the patents and the patent applications cited herein.

Location sensor 126 is configured to transmit a signal to console 120 that is indicative of the location coordinates of distal end 114. Location sensor 126 can include one or more miniature coils, and typically can include multiple coils oriented along different axes. Alternatively, location sensor 126 can comprise either another type of magnetic sensor, or position transducers of other types, such as impedance-based or ultrasonic location sensors.

Catheter 110 can also include a force sensor 128 contained within distal end 114. Force sensor 128 can measure a force applied by distal end 114 to the endocardial tissue of heart 103 and generate a signal that is sent to console 120. Force sensor 128 can include a magnetic field transmitter and a receiver connected by a spring in distal end 114, and can generate an indication of the force based on measuring a deflection of the spring. Further functional details of the catheter and force sensor are described in U.S. Patent Application Publication No. 2009/0093806, which issued as U.S. Pat. No. 8,357,152 on Jan. 22, 2013, and U.S. Patent Application Publication No. 2009/0138007, which issued as U.S. Pat. No. 8,535,308 on Sep. 17, 2013, and are incorporated herein by reference as if fully set forth. Alternatively, distal end 114 can include another type of force sensor that can use, for example, fiber optics or impedance measurements.

Catheter 110 can include an electrode 130 coupled to distal end 114 and configured to function as an impedance-based position transducer. Additionally or alternatively, electrode 130 can be configured to measure a certain physiological property, for example the local surface electrical potential of the cardiac tissue at one or more of the multiple locations. Electrode 130 can be configured to apply radio frequency (RF) energy to ablate endocardial tissue in heart 103.

Although example medical system 100 can be configured to measure the position of distal end 114 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126, 6,456,864 and 5,944,022, and are incorporated herein by reference as if fully set forth.

Signal processor 140 can be included in a general-purpose computer, with a suitable front end and interface circuits for receiving signals from catheter 110 and controlling the other components of console 120. Signal processor 140 can be programmed, using software, to carry out the functions that are described herein. The software can be downloaded to console 120 in electronic form, over a network, for example, or it can be provided on non-transitory tangible media, such as optical, magnetic or electronic memory media. Alternatively, some or all of the functions of signal processor 140 can be performed by dedicated or programmable digital hardware components.

In the example of FIG. 1, console 120 can also be connected by a cable 150 to external sensors 152. External sensors 152 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic location sensors to locate catheter 110 during use. Although not shown in FIG. 1, external sensors 152 can be embedded in a vest that is configured to be worn by patient 102. External sensors 152 can aid in identifying and tracking the respiration cycle of patient 103. External sensors 152 can transmit information to console 120 via cable 150.

Additionally, or alternatively, catheter 110, and external sensors 152 can communicate with console 120 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth®, acoustic or other transmissions.

Catheter 110 can be equipped with a wireless digital interface that can communicate with a corresponding input/output (I/O) interface 160 in console 120. Wireless digital interface and the I/O interface 160 can operate in accordance with any suitable wireless communication standard that is known in the art, such as IR, RF, Bluetooth, one of the IEEE 802.11 families of standards, or the HiperLAN standard. External sensors 152 can include one or more wireless sensor nodes integrated on a flexible substrate. The one or more wireless sensor nodes can include a wireless transmit/receive unit (WTRU) enabling local digital signal processing, a radio link, and a power supply such as miniaturized rechargeable battery.

Wireless digital interface and the I/O interface 160 can enable console 120 to interact with catheter 110 and external sensors 152. Based on the electrical impulses received from external sensors 152 and signals received from catheter 110 via wireless digital interface and the I/O interface 160 and other components of medical system 100, signal processor 140 can generate information 105 which can be shown on a display 170.

During the diagnostic treatment, signal processor 140 can present information 105, and/or can store data in a memory 180. Memory 180 can include any suitable volatile and/or non-volatile memory, such as random access memory or a hard disk drive.

Catheter control unit 112 can be configured to be operated by an operator 130 to manipulate catheter 110 based on information 105, which is selectable using one or more input devices 185. Alternatively, medical system 100 can include a second operator that manipulates console 120 while operator 130 operates catheter control unit 112 to manipulate catheter 110 based on information 105. The second operator can also be provided with information 105. The mechanics of the construction and use of catheter control device 112 to move and position distal end 114 of catheter 110 is within the state of the art such as employed in the CARTO™ mapping system referenced above. For example, see also U.S. Pat. No. 6,690,963 which is incorporated herein by reference as if fully set forth.

Figure 2:
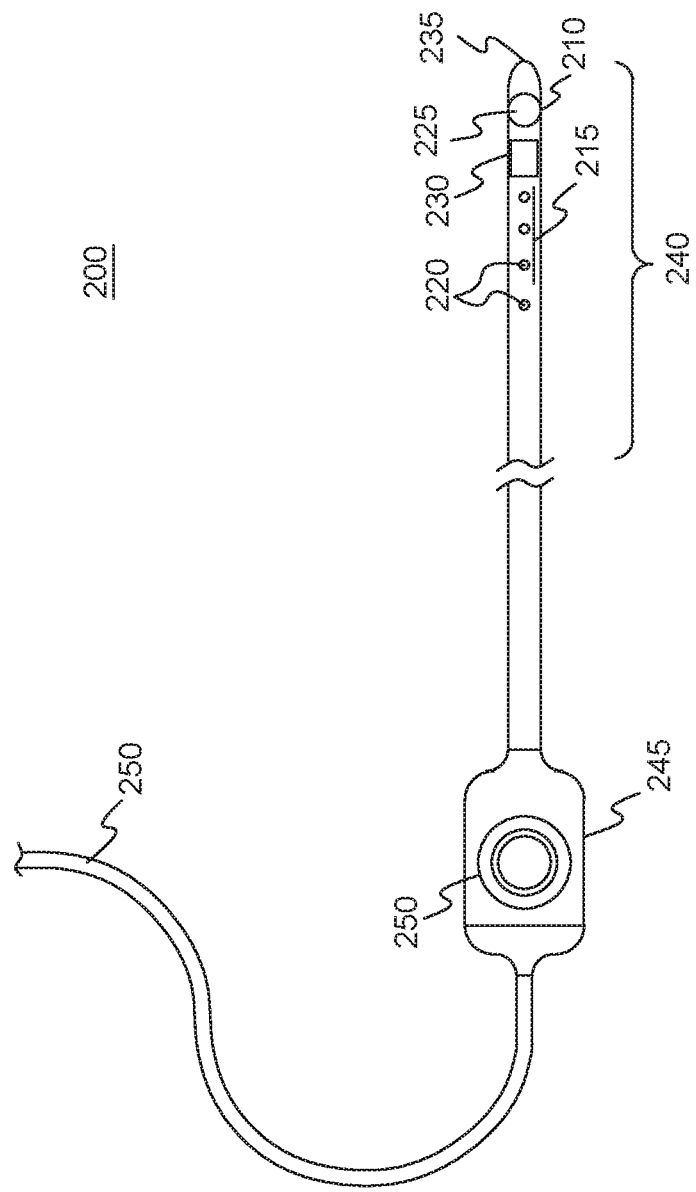
FIG. 2 is a schematic diagram of an example catheter in accordance with certain implementations.
Figure 3:
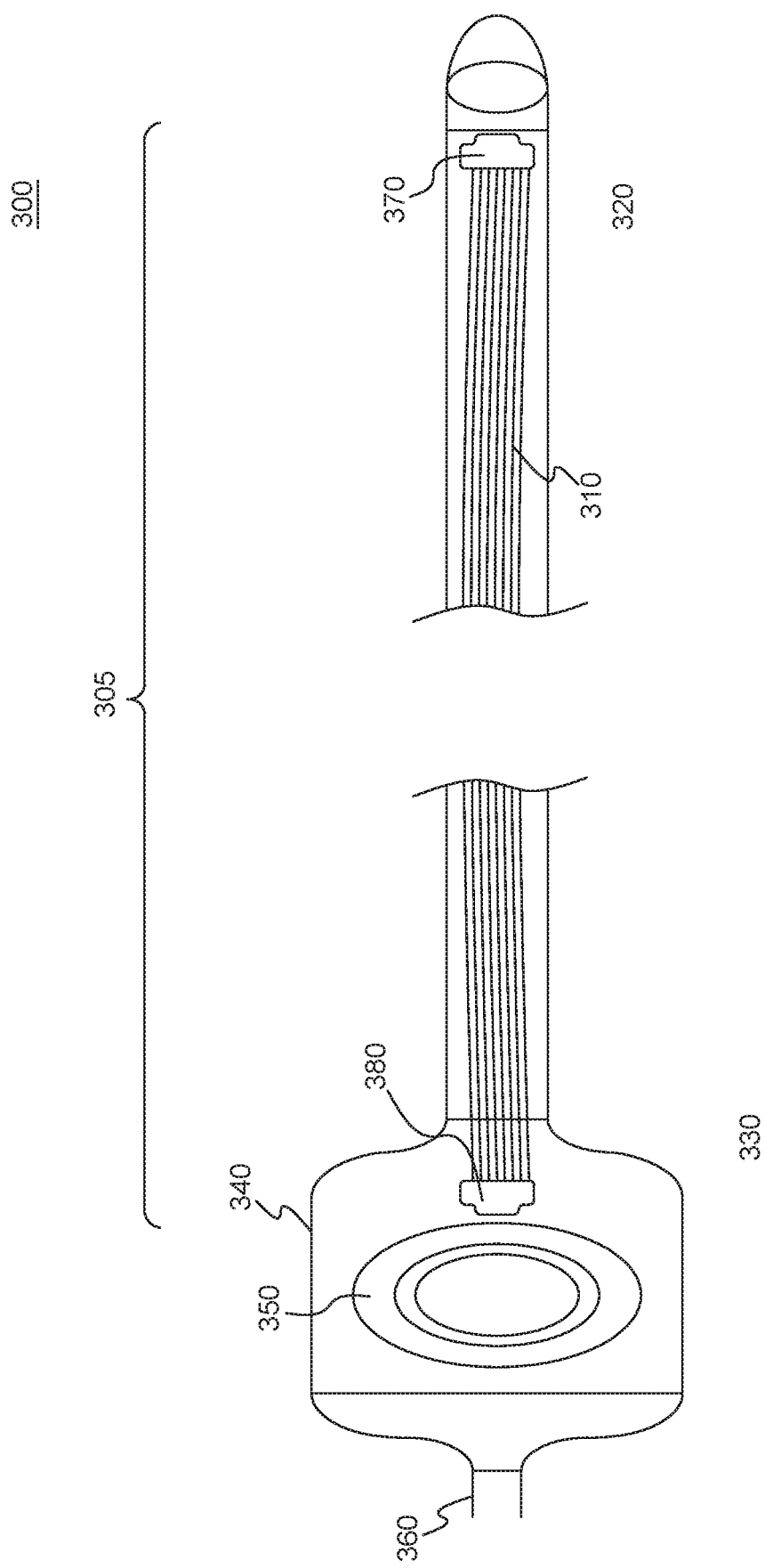
FIG. 3 is a schematic diagram of an example catheter with a printed ribbon in accordance with certain implementations.

An example catheter 200 is shown in greater detail in FIG. 2, showing some, but not all, of the elements that may be included in catheter 200. A catheter 200 may include, but is not limited to include, any one or more of the following components: electrode(s) 210; temperature sensor(s) 215; non-contact electrodes 220; image sensor(s) 225; positioning or location sensor(s) 230; distal tip 235; distal end 240; handle 245; and/or cable 250. The schematic diagram of catheter 200 in FIG. 3 is a high-level representation of possible components of catheter 200, such that the location and configuration of the components in catheter 200 may be different than shown.

Distal end 240 of catheter 200 may include an electrode(s) 210 at distal tip 235 that may be used to measure electrical properties of the cardiac tissue. Electrode(s) 210 may also be used to send electrical signals to the heart for diagnostic purposes. Electrode(s) 210 may also perform ablation on defective cardiac tissue by applying energy (e.g., RF energy) directly to the cardiac tissue at the desired location of ablation.

Distal end 240 of catheter 200 may include temperature sensor(s) 215 to measure the temperature of the cardiac tissue in contact with distal end 240 and/or measure the temperature of distal end 240 itself. For example, thermocouples or thermistors for measuring temperature may be placed anywhere along distal end 240 to serve as temperature sensor(s) 215.

Distal end 240 may include non-contact electrodes 220 arranged in an array, which may be used to simultaneously receive and measure far-field electrical signals from the walls of the heart chamber of a patient. Electrode(s) 210 and non-contact electrodes 220 provide information regarding the electrical properties of the heart to processing device(s) for processing, such as for example, signal processor 140.

Catheter(s) 200 may be equipped with one or more image sensor(s) 225, such as a charge coupled device (CCD) image sensor, and/or a camera for capturing endoscopic images when inserted in a body cavity. Image sensor(s) 225 may be located at distal end 240.

Distal end 240 may include location sensor(s) 230 in distal tip 235 of catheter 200 that may generate signals used to determine the position and orientation (and/or distance) of catheter 200 in the body. In an example, the relative position and orientation of location sensor(s) 230, electrode(s) 210, and distal tip 235 are fixed and known in order to facilitate accurate positioning information of distal tip 235. For example, the position of location sensor(s) 230 may be determined in part based on the relative position to known positions outside the heart (e.g., based on extra-cardiac sensors). The use of location sensor(s) 230 may provide improved location accuracy within the magnetic fields in the surrounding space and provide location information that is adaptable to patient movement because the position information of catheter 200 is relative to the anatomy of the patient.

Handle 245 of catheter 220 may be operated by an operator such as a physician and may include controls 250 to enable the physician to effectively steer distal tip 235 in the desired direction.

Electrodes 210, 220, and sensors 215, 225, 230 may be connected to processing device(s), such as for example signal processor 140, via wires that may pass through handle 245 and cable 250, in order to provide information, such as location, electrical, imaging and/or temperature information, to a console system, which may be used to operate and display the function of catheter 200 within the heart in real-time.

FIG. 3 is a schematic diagram of an example catheter 300 with a printed flexible substrate 310 in accordance with certain implementations. Catheter 300 includes a catheter shaft 305, a handle 340 and a cable 360. Catheter shaft 305 includes a distal end 320 and a proximate end or handle end 330. Distal end 320 includes a number of sensors (not shown) as described herein. Proximate end 330 ends at handle 340. Handle 340 includes controls 350 and a cable 360 which connects to processing devices in a console, for example, console 120. Printed flexible substrate 310 includes distal end connectors 370 and proximate end connectors 380. Printed flexible substrate 310 extends from distal end 320 to proximate end 330. In particular, distal end connectors 370 are connected to sensors and proximate end connectors 380 are connected to cable 360 via cards or connectors in handle 340.

Figure 4:
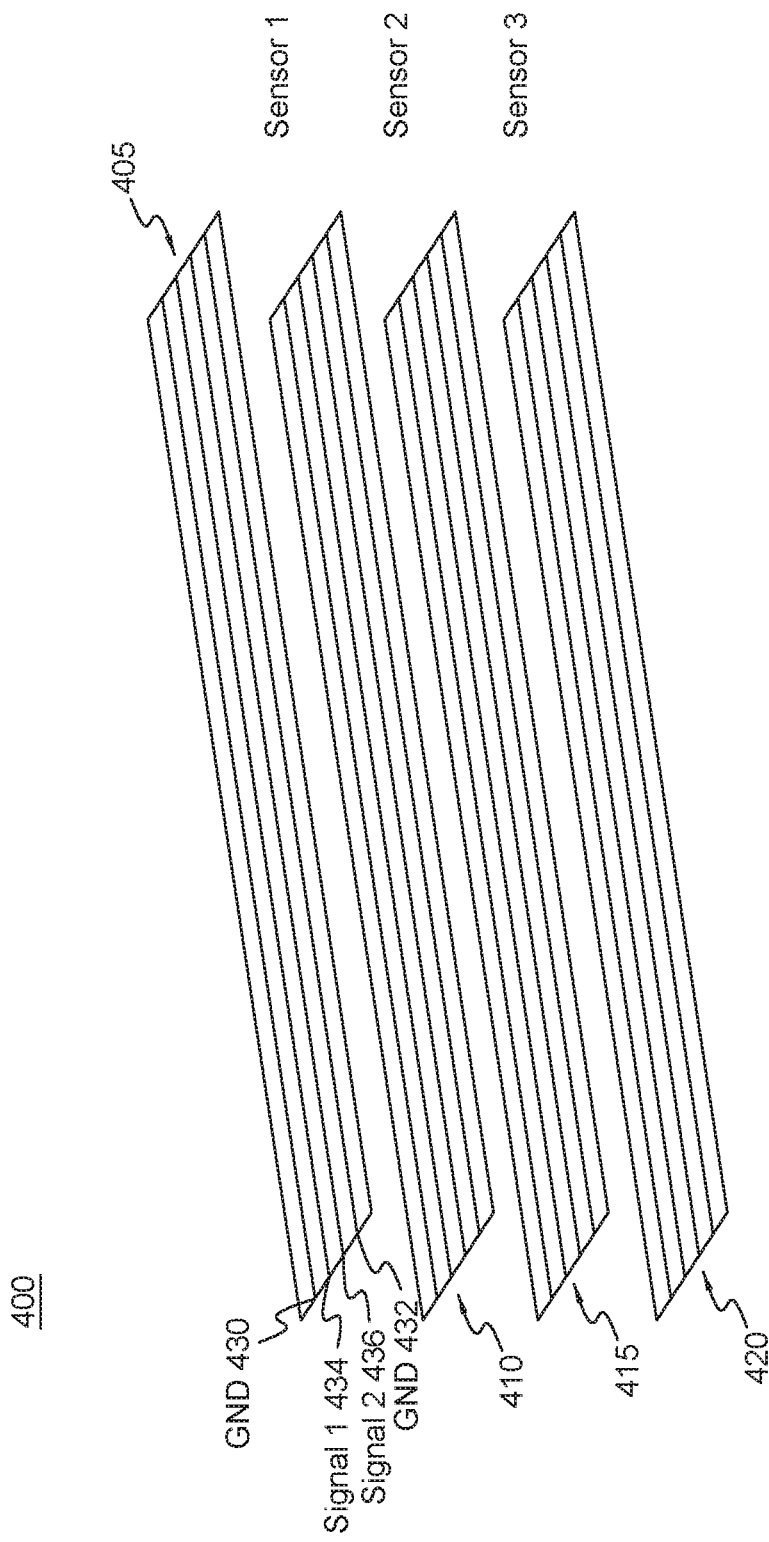
FIG. 4 is an example printed ribbon in accordance with certain implementations.

FIG. 4 is an example printed flexible substrate 400 in accordance with certain implementations. Printed flexible substrate 400 can be any type of flexible substrate including a flexible printed circuit board (PCB), a ribbon and other similar structures. Printed flexible substrate 400 can include a predetermined number of layers which may depend on the type of sensor in the catheter. The predetermined number of layers can include signal layers and reference layers. For example, the sensor can be a location sensor which includes three coils, one for each of an X, Y and Z axis. In an illustrative example, signal layers can include layers 410, 415 and 420, which are associated with coils representing each X, Y and Z axis. As noted herein, a reference layer, e.g., layer 405, may be needed for magnetic interference cancellation that results from other devices in the catheter or the medical system.

In an implementation, each of layers 405, 410, 415, and 420 can include any number of traces. The traces may include signal traces and ground traces. In an implementation, the traces can include ground traces 430 and 432, a first signal trace 434 and a second signal trace 436. Each of the traces, e.g., ground traces 430 and 432, first signal trace 434 and second signal trace 436, is made of a conductive material, such as copper, gold, gold cladded copper or other similar materials. The conductive material is deposited, printed or otherwise positioned on the flexible substrate. Measurements from each of layers 405, 410, 415, and 420 are eventually routed to processing device(s) such as for example signal processor 140 and signal processing hardware such as amplifiers and filters.

As noted above, reference layer 405 is configured to measure magnetic radiation that may cause interference in the measurements carried by first signal trace 434 and second signal trace 436 and in the respective signal layers in layers 410, 415 and 420. In an implementation, reference layer 405 is shorted and measures the magnetic fields that cause the magnetic interference. This information is then used by processing device(s) such as for example signal processor 140 and signal processing hardware to cancel out the magnetic interference from the measurements carried by the signal layers, e.g., layers 410, 415 and 420.

FIG. 5 is an example printed flexible substrate 550 wrapped with respect to a catheter 500 in accordance with certain implementations. Catheter 500 can include a catheter shaft 510 and a handle 520. Catheter shaft 510 includes a distal tip 530 which includes a sensor 540 as shown in FIG. 5A. Handle 520 includes an electronic card 525, which may include filters, signal amplifiers, and analog-to-digital converters for signal processing. A printed flexible substrate 550 can be implemented as shown in FIG. 4 and then wrapped around a catheter shaft 510. One end of printed flexible substrate 550 is connected to sensor 540 and another end of printed flexible substrate 550 is connected to electronic card 525. In an implementation, in addition to and in conjunction with the configuration illustrated in FIG. 3, a printed flexible substrate 550 can be wrapped around an irrigation tube, for example, inside of catheter shaft 510 for sensors that do not use magnetic based devices.

Figure 6:
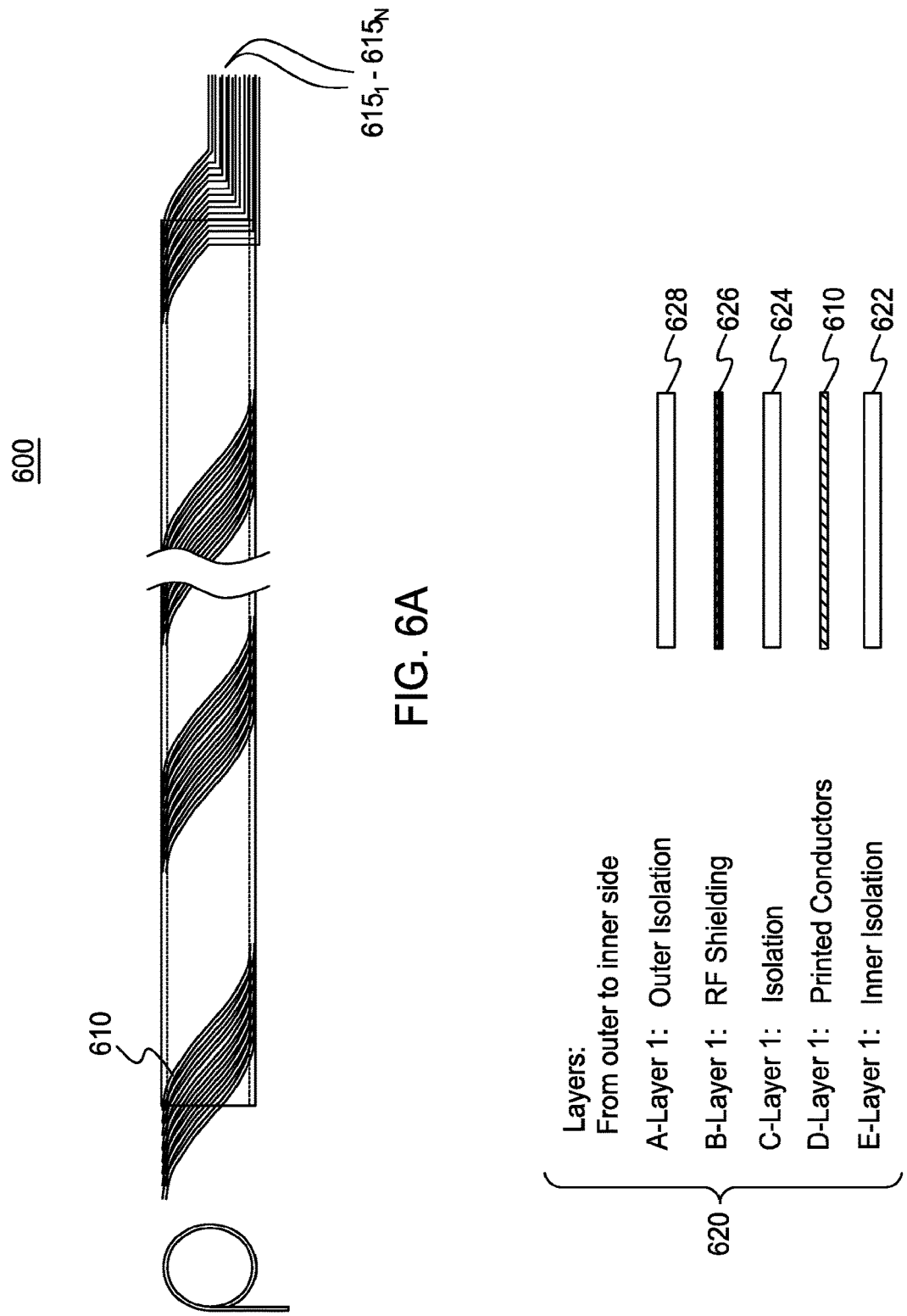
FIG. 6A is an example printed ribbon wrapped around a catheter in accordance with certain implementations.
FIG. 6B is an example cross-section of the example printed ribbon of FIG. 6A in accordance with certain implementations.

FIG. 6A shows more detail for the configuration illustrated in FIG. 5 and FIG. 6B shows a cross-section of the configuration shown in FIG. 6A. FIG. 6A shows a catheter shaft 600 that has a printed flexible substrate 610 wrapped with respect to catheter shaft 600 in accordance with certain implementations. Printed flexible substrate 610 includes multiple layers $615_1$-$615_N$, which carry signals from the sensors to the processing device(s). A shaft cross section 620 shows the layer structures where an inner layer 622 is built with isolation material. Conductor layers (i.e. printed flexible substrate) 610 is printed and isolated from a shielding layer 626 by an isolation layer 624. The shielding layer 626 is isolated by a nonconductive layer 628. The printed conductors/traces are applied in a spiral shape to enable flexibility of the shaft 600.

Figure 7:
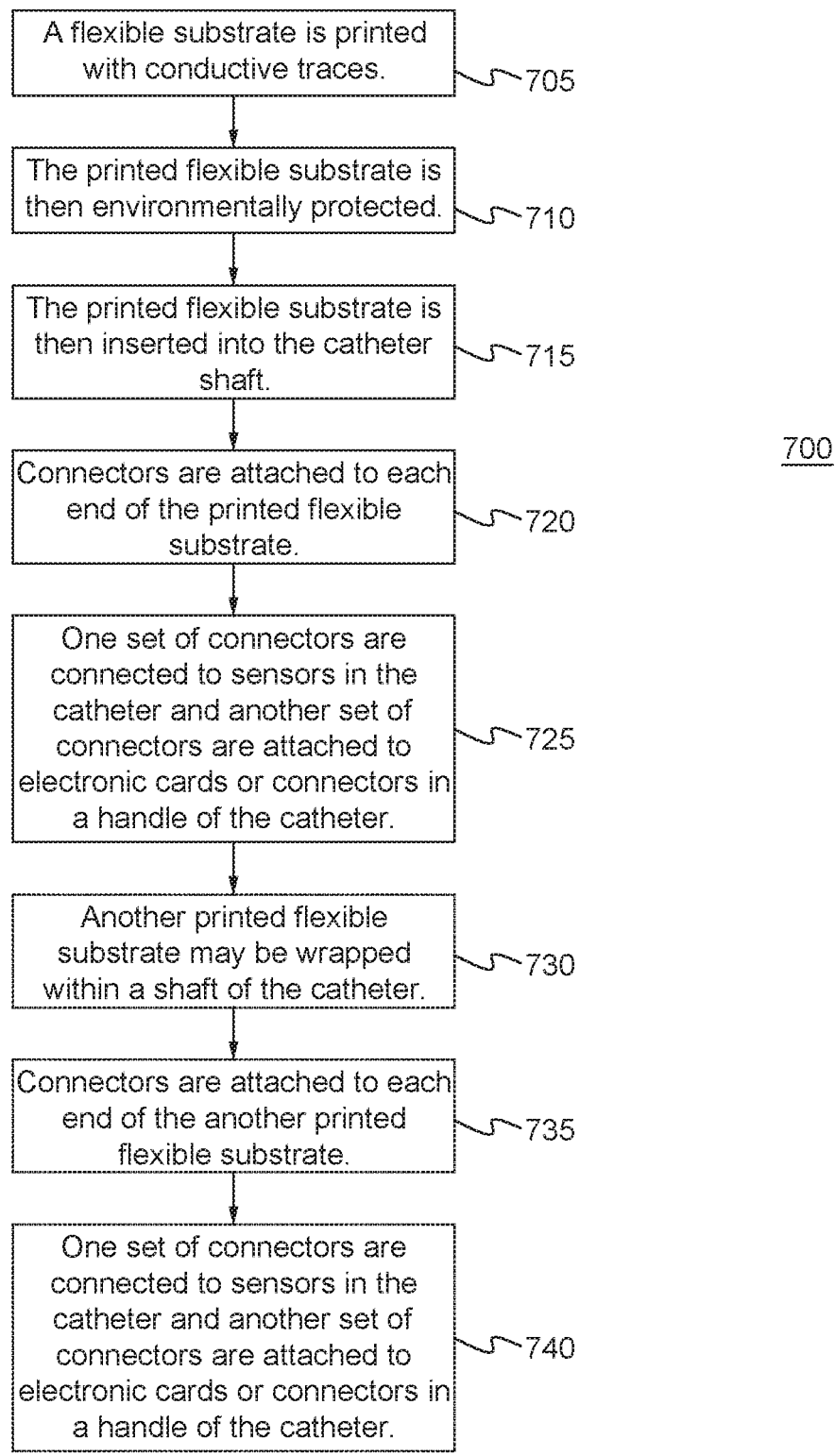
FIG. 7 is a method for assembling a catheter in accordance with certain implementations.

FIG. 7 is a method 700 for assembling a catheter in accordance with certain implementations. A flexible substrate is printed with conductive traces (705). Each printed flexible substrate can include multiple layers or levels. The printed flexible substrate is then environmentally protected (710). For example, the printed flexible substrate can be laminated. The printed flexible substrate is then inserted into the catheter shaft (715). Connectors are attached to each end of the printed flexible substrate (720). One set of connectors are connected to sensors in the catheter and another set of connectors are attached to electronic cards or connectors in a handle of the catheter (725). In an implementation, another printed flexible substrate may be wrapped with respect to a shaft of the catheter (730). Connectors are attached to each end of the another printed flexible substrate (735). One set of connectors are connected to sensors in the catheter and another set of connectors are attached to electronic cards or connectors in a handle of the catheter (740).

In general, a method for catheter assembly includes printing conductive traces on at least one flexible substrate, encapsulating the at least one flexible substrate for environmental protection, inserting at least one encapsulated flexible substrate into a catheter shaft of a catheter, attaching connectors to each end of the at least one encapsulated flexible substrate, attaching a set of connectors to sensors located at a distal end of the catheter, and attaching another set of connectors to electronics in a handle of the catheter. In an implementation, the method includes wrapping an encapsulated flexible substrate around a component contained within the catheter shaft, attaching connectors to each end of the encapsulated flexible substrate, attaching a set of connectors to non-magnetic based sensors in the catheter, and attaching another set of connectors to electronics in a handle of the catheter. In an implementation, the at least one flexible substrate includes a plurality of layers, each layer having a plurality of conductive traces. In an implementation, the plurality of layers includes a reference layer, and the method further includes shorting two of the plurality of conductive traces in the reference layer to measure magnetic radiation for interference cancellation determination. In an implementation, the plurality of layers includes signal layers that are connected to the sensors. In an implementation, the encapsulating step includes at least laminating the at least one flexible substrate. In an implementation, the at least one encapsulated flexible substrate is rolled prior to insertion into the catheter shaft. In an implementation, the at least one encapsulated flexible substrate is inserted substantially linear into the catheter shaft. In an implementation, the conductive traces include signal traces and ground traces.

In general, a catheter includes a catheter shaft having a distal end and a handle. The catheter further includes sensors located at the distal end, electronics located at the handle and at least one flexible substrate which is inserted inside the catheter shaft, where the at least one flexible substrate has conductive traces. The catheter further includes a first connector which connects the sensors to one end of the at least one flexible substrate and a second connector which connects the electronics to another end of the at least one flexible substrate. The first connector and the second connector are connected after insertion into the catheter shaft. In an implementation, the at least one flexible substrate is encapsulated for environmental protection. In an implementation, the catheter further includes non-magnetic sensors, another flexible substrate that is wrapped around a component in the catheter shaft, a third connector which connects the non-magnetic sensors to one end of the another flexible substrate and a fourth connector which connects the electronics to another end of the flexible substrate. In an implementation, the at least one flexible substrate includes a plurality of layers, each layer having a plurality of conductive traces. In an implementation, the plurality of layers includes a reference layer, where two of the plurality of conductive traces are shorted in the reference layer to measure magnetic radiation for interference cancellation determination. In an implementation, the plurality of layers includes signal layers that are connected to the sensors. In an implementation, the at least one flexible substrate is laminated for environmental protection. In an implementation, the at least one flexible substrate is rolled prior to insertion into the catheter shaft. In an implementation, the at least one flexible substrate is positioned substantially linear into the catheter shaft. In an implementation, the conductive traces include signal traces and ground traces.

The description herein is with respect to cardiac mapping and ablation procedures for a cardiac system, although it is understood by one skilled in the art that the disclosures may be applied to systems and procedures that can be used in any cavity or system in the body, including, but not limited to, the respiratory/pulmonary system, the respiratory and pulmonary system, the digestive system, the neurovascular system, and/or the circulatory system.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A catheter comprising:
a catheter shaft having a distal end and a handle;
sensors located at the distal end;
non-magnetic sensors;
electronics located at the handle;
at least one flexible substrate inserted inside the catheter shaft, the at least one flexible substrate having conductive traces;
another flexible substrate that is wrapped around a component in the catheter shaft;
a first connector, the first connector connecting the sensors to one end of the at least one flexible substrate;
a third connector, the third connector connecting the non-magnetic sensors to one end of the another flexible substrate; and
a second connector and a fourth connector, the second connector and the fourth connector both connecting the electronics to another end of the at least one flexible substrate,
wherein the first connector and the second connector are connected after insertion into the catheter shaft.

2. The catheter of claim 1, wherein the at least one flexible substrate is encapsulated for environmental protection.

3. The catheter of claim 1, wherein the at least one flexible substrate includes a plurality of layers, each layer having a plurality of conductive traces.

4. The catheter of claim 3, wherein the plurality of layers includes a reference layer, wherein two of the plurality of conductive traces are shorted in the reference layer to measure magnetic radiation for interference cancellation determination.

5. The catheter of claim 4, wherein the plurality of layers includes signal layers that are connected to the sensors.

6. The catheter of claim 1, wherein the at least one flexible substrate is laminated for environmental protection.

7. The catheter of claim 1, wherein the at least one flexible substrate is rolled prior to insertion into the catheter shaft.

8. The catheter of claim 1, wherein the at least one flexible substrate is positioned substantially linear into the catheter shaft.

9. The catheter of claim 1, wherein the conductive traces include signal traces and ground traces.

* * * * *